United States Patent [19]

Kulakowski

[11] Patent Number: 5,016,636
[45] Date of Patent: May 21, 1991

[54] BELT FOR RETAINING SENSING ELECTRODES ON THE CHEST OF AN INFANT AFFLICTED WITH APNEA

[76] Inventor: Phyllis Kulakowski, 16 Tucker's Ct., Peabody, Mass. 01960

[21] Appl. No.: 363,921

[22] Filed: Jun. 8, 1989

[51] Int. Cl.$^5$ .............................................. A61B 5/408
[52] U.S. Cl. .................................... 128/644; 128/384; 128/700
[58] Field of Search ............... 128/644, 698, 384, 385, 128/716, 798, 700, 802, 670, 671

[56] References Cited

U.S. PATENT DOCUMENTS

| | | | |
|---|---|---|---|
| 424,827 | 4/1890 | Shelton | 128/385 |
| 4,072,145 | 2/1978 | Silva | 128/644 |
| 4,082,087 | 4/1978 | Howson | 128/640 |
| 4,090,504 | 5/1978 | Nathan | 128/670 |
| 4,381,012 | 4/1983 | Russek | 128/802 |
| 4,895,162 | 1/1990 | Dolliver | 128/384 |

OTHER PUBLICATIONS

A Handbook for Infant Monitoring, 1984, by Healthdyne Inc. and Terry Koepsell, p. 28.

Primary Examiner—Lee S. Cohen
Assistant Examiner—Scott M. Getzow
Attorney, Agent, or Firm—Owen J. Meegan

[57] ABSTRACT

A belt for securing sensing electrodes to the chest of an infant afflicted with Apnea. The belt comprises an elongated band of fabric of sufficient length to encircle and to be fastened around the chest of the infant. The band has an inner side, an outer side and two ends. A tunnel is disposed on the inner side of the band and is adapted to removably receive and house wires for connecting sensing electrodes to an Apnea monitor. Two ports are disposed at the ends of the tunnel and arranged to allow wires to extend from the band and be connected to the monitor. Another port is disposed centrally of the band and arranged to form a port and allow wires to extend from the band to connect to the sensing electrodes. To fasten the belt to the infant, an interrelatable, two component, adjustable fastener is disposed on each end of the band. One of the two components of the fastener is disposed on the inner side of the band and the other is disposed on the outer side, whereby each component of the fastener can overlap and attach to form an adjustable belt that can be fastened over the back of the infant and provide for disposition of sensing electrodes on the chest of infant.

7 Claims, 1 Drawing Sheet

U.S. Patent    May 21, 1991    5,016,636 ature of the invention

BELT FOR RETAINING SENSING ELECTRODES ON THE CHEST OF AN INFANT AFFLICTED WITH APNEA

BACKGROUND OF THE INVENTION

Field of the Invention

The present invention relates to a device for securing electrodes to the chest of an infant afflicted with Apnea. Specifically, the present invention relates to an adjustable belt for disposition about the chest of an infant to support sensing electrodes that have to be disposed there to monitor heartbeat and respiration.

Infants afflicted with Apnea require constant monitoring in the home to identify abnormal pauses in breathing and changes in heart rate. A cessation of breathing, called Apnea, may be accompanied by either a slowing or an increase of the infant's heart rate. These are detectable events. These conditions can result in low supplies of oxygen in the infant's system. To determine if an infant's heart or respiratory rate has changed, physicians place the infants on monitoring devices which detect these changes and inform the observers, frequently the parents, of possible threatening episodes in sufficient time for corrective action to be taken.

In the monitoring devices, lead wires are used to conduct electrical impulses detected by the sensing electrodes. The electrodes are firmly placed upon the infant's chest. The lead wires are plugged into the monitor and the electrodes transmit breathing or heartbeat signals through the lead wires. Commonly, two types of electrodes are used. Disposable electrodes snap on to the lead wires and are pads or discs made of paper or foam rubber which stick to the infant with a special gel that maximizes the quality of the contact with the skin. Permanent electrodes are similar in concept but are detachably affixed to the belt. The electrodes and the belt have hook and loop fasteners which co-act with the electrodes to hold the electrodes in place against the infant's chest. The belt secures the electrodes in place.

In the prior art, the electrode belt has been made of a length of elasticized material such as a stretchable foam. The belt is frequently secured around the infant with a fastening device made of plastic hooks and loops that mesh together and form a detachable fastener. Once the infant is attached to the monitor using the belt of the prior art, alarms occur frequently. Usually these alarms are "false alarms" and result from mechanical malfunctions such as loose leads or from lead wire connections or from an electrode not contacting the skin. The parent, however, must respond to the false alarm as if a real episode were occurring. Very frequently, the false alarms occur when the infant reaches and grasps the electrodes or the lead wires and either disconnects them from the monitor or from its body. Also, as the infant moves during the night while sleeping, the wires can become tangled in the infant's arms and disconnect the lead wires from the monitor. All of such interruptions give a false alarm signal to which the parent must respond.

SUMMARY OF THE INVENTION

The present invention provides an elongated band of fabric that has sufficient length to encircle the infant and to be fastened around its chest. A tunnel is formed on the inner side along the length of the band to receive and house the wires that are connected to the sensing electrodes. The tunnel is preferably formed by sewing the edge of a fold of the band to the center of the band. At about the middle of the band, the fold is not sewn to the band so as to provide for egress of the wires. In the preferred embodiment, the fold is sewn over the entire length of the band with only the central section remaining unsewn thereby to form a central port. In that way, wires can emerge from both ends of the tunnel, and when the band is properly secured around the infant, they will emerge from the belt over the infant's back. Thus, the infant cannot readily grasp and detach them from the monitor.

A fastener device is disposed on the ends of the band and in the preferred embodiment, the fastener is an interrelatable, two component adjustable fastener, preferably in the form of pads of the well known plastic hooks and loops which have a pad of hooks that join with a pad of loops to snugly secure the fastener together. The belt is thus adjustable so as to compensate for growth and infants of various sizes.

DESCRIPTION OF THE PREFERRED EMBODIMENT

Figure 1:
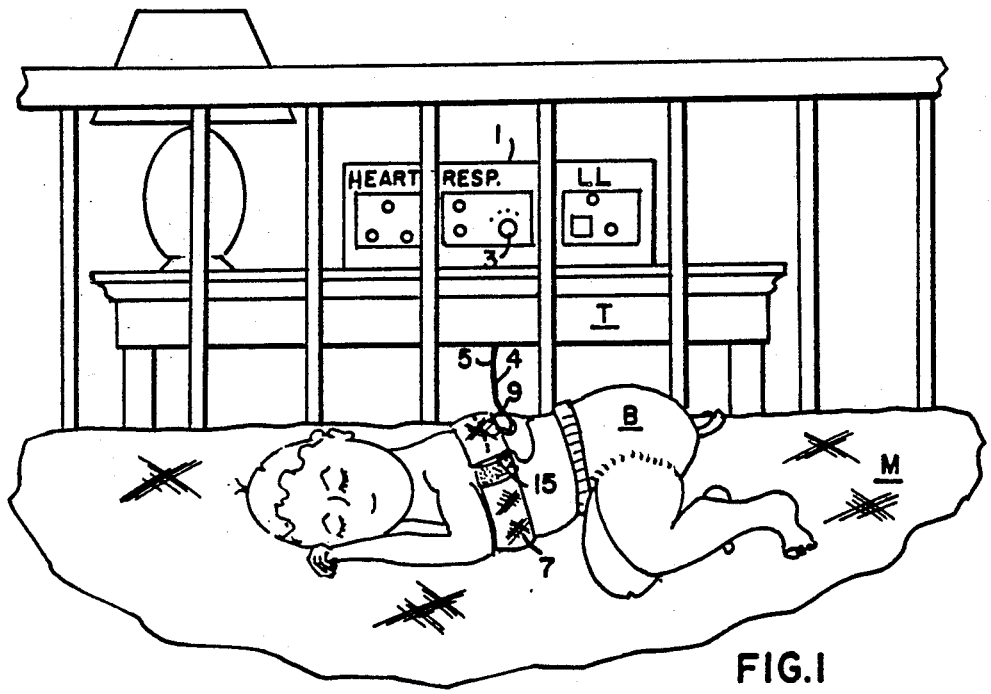
FIG. 1 is a side elevational view of an infant in a crib with the belt of the present invention disposed about its chest and with the wires attached to an Apnea monitor.

Referring to FIG. 1, a infant B is shown lying on its stomach on a mattress M with a monitor 1 disposed on a table T. The monitor 1 is of conventional design and may be a Health-Dyne Infant Monitor 16900, as sold by Health-Dyne Inc. of Marietta, Ga. The monitor includes a heart monitor (under the legend "HEART") in upper left corner of the front panel that blinks with each heartbeat. The light is on during the heartbeat and is off during the rest period between beats. A respiration monitor (under the legend "RESP.") is located in the upper center of the front panel and blinks as the infant breathes. An alarm delay setting 3 is associated with the respiration monitor and a setting determines the number of seconds allowed to pass from the time an infant stops breathing until an Apnea alarm sounds. A loose lead signal (under the legend L.L.) is located in the upper right corner of the front panel. A light is associated with the loose lead signal and an alarm will sound if poor contacts occur between the electrodes and the infant, if the electrode belt is too loose, if the electrodes are faulty, if the lead wires are faulty, or if poor contacts exist at the connections.

As shown in the drawing, the infant B is lying on a mattress M. The infant B is attached to the monitor 1 by means of two lead wires 4 and 5. Each of these wires emerge from a tunnel 9 in a belt 7 that is wrapped around the infant's chest. As shown in the Figure, the tunnel 9 ends in a port 15 from the which a wire emerges and another that is not shown in FIG. 1. Tunnel 9 preferably extends around the entire length of the belt 7 and one of the wires 4 emerges from one of the ports and the other wire 5 emerges from the other port. As shown, the belt 7 is wrapped so that the wires can emerge from a location adjacent the infant's back. The two ends of the belt 7 are joined together with a conventional hook and loop fastening device with one of the elements disposed on the outer side of the belt 7 and the other element of the fastener disposed on the inner side of the belt 7.

Figure 2:
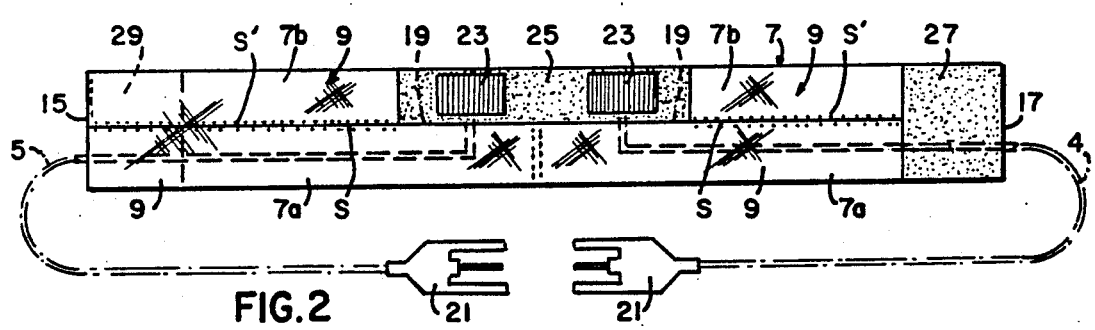
FIG. 2 is an elevational view of the inner side of the Apnea belt.
Figure 3:
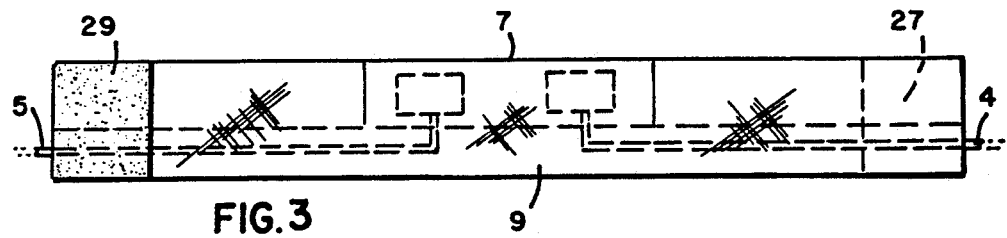
FIG. 3 is an elevational view of the outer side of the Apnea belt.

Referring now to FIGS. 2 and 3, the belt 7 is shown flat and with the inner and outer sides displayed. The belt 7, as is shown in the drawing, is longer than it is wide and has a fold 7a running along its entire length. Fold 7a is attached to belt 7 by stitches S to form the tunnel 9. The ends of fold 7a are not stitched to the belt 7 thereby forming the ports 15 and 17. Also, a central section 19 of the fold 7a forming tunnel 9 is not stitched to the belt 7 either. In this way, the tunnel 9 receives and houses the wires 4 and 5. Preferably, the ports 15 and 17 are wide enough to accommodate electrical connectors 21 and/or electrodes 23 so that either of these devices can be threaded through the tunnel 9. The electrodes 23 are passed through the port formed by central section 19 of the fold 7a so that they can be disposed on the infant's body.

A second fold 7b is stitched with stitches S' to belt 7 along its length. The stitches S' are extended over the ends of the belt 7 and a fastener pad 25 formed of the plastic loops is stitched to the second fold 7b. The second fold 7b gives strength to the belt 7. When an infant is being monitored using permanent electrodes, these devices are sold with fasteners formed of pads of hooks disposed on their backs (not shown) that can mate with the loop fastener pad 25 and be firmly attached thereto.

In FIG. 3 the reverse side of the belt 7 is shown. A fastener pad 29 is disposed at the left side of the belt 7 and will mate with the fastener pad 27 on the right to provide a snug fit of the belt around the infant so as to insure the contact of the electrodes to the infant's chest.

In the preferred embodiment, the belt 7 is designed of double faced quilted material, generally 50% cotton and 50% polyester for the infant's comfort. It is preferably 3½ inches wide. The loop pad of the fastener 25 is 2 inches in width and 7 inches in length so that permanent electrodes with hook fasteners affixed to their backs will adhere to it. Having a loop pad on the second fold 7b is preferable since only soft fabric or the soft loops touch the infant's skin. The port in central section 19 is preferably about 2 inches in length so that the lead wires 4 and 5 can be pulled through the two inch opening. Preferably one lead wire 4 is used for the right side of the belt 7 and the other lead wire 5 is used for the left. The belt is 22 inches long and the hook and loop fastening pads 27 and 29 are 4 inches in length by 3½ inches in width (which is the width of the belt itself so as to allow the belt to be enlarged easily to provide for adjustability).

Since the lead wires exit from the belt at the rear, an infant's tugging at the lead wires or loosening the wires with movement is markedly reduced, thereby reducing the number of "false alarms". Also since a fabric is used, it can be washed frequently without having it stretch out of shape or lose its stretch, as was the case with belts made of stretchable foam.

It is apparent that modifications and changes can be made within the spirit and scope of the present invention, but it my intention, however, only to be limited by the scope of the appended claims.

As my invention, I claim:

1. A belt for securing sensing electrodes to the chest of an infant afflicted with Apnea, said belt comprising:
   an elongated band of fabric of sufficient length to encircle and to be fastened around the chest of said infant, said band having an inner side and an outer side and two ends;
   tunnel means disposed on said band, said tunnel means extending over the length of said band and adapted to removably receive and house wires for connecting sensing electrodes to a monitor,;
   first and second port means disposed on said tunnel means, said first port means being formed as openings at each end of said tunnel means to allow wires to extend from each of the ends of said tunnel means and be connected to said monitor, said second port means disposed centrally about said band, said second port means being arranged to allow wires to extend from said band to connect to said sensing electrodes;
   an interrelated, two component, adjustable fastener means disposed on each end of said band, one of the two components of said fastener means being disposed on the inner side of said band and the other of said components being disposed on the outer side of said band, whereby the components of the fastener means can overlap and attach to each other to form an adjustable belt that can be fastened over the back of the infant and provide for disposition of said sensing electrodes on the chest of said infant and whereby said wires can emerge from a rear of the belt when worn.

2. The belt according to claim 1 further including sensing electrode fastening means disposed centrally on the inner side of said band whereby to provide for attachment of said sensing electrodes to said band.

3. A belt for securing sensing electrodes to the chest of an infant afflicted with Apnea, said belt comprising;
   an elongated band of fabric of sufficient length to encircle and be fastened around the chest of said infant, said band having an upper edge, a lower edge, an inner side and an outer side and two ends;
   a first fold of said band of fabric, said first fold extending from said lower edge and being folded over said inner side of said band and being attached to the center of said band so as to form a tunnel between the first fold and the inner side of said band, whereby to removably receive and house wires for connecting sensing electrodes to a monitor;
   said fold being attached to said band to form a first and a second port means, said first port means being disposed at the end of said band and arranged to allow wires to extend from said band and be connected to said monitor, said second port means disposed centrally of said band, said second port means being arranged to allow wires to extend from said band to connect to said sensing electrodes; and
   interrelatable, two component, adjustable fastener means disposed on each end of said band, one of the two components of said fastener means being disposed on the inner side of said band and the other of the components being disposed on the outer side of said band, whereby each component of said fastener means can overlap and attach to each other to form an adjustable belt that can be fastened over the back of the infant and provide for secure disposition of said sensing electrodes on the chest of said infant.

4. The belt according to claim 3 wherein the first fold extends over the entire length of said band and said first port means is formed as openings at each end of said band whereby to allow an individual wire to extend from each of the ends of said band.

5. The belt according to claim 3 further including sensing electrode fastening means disposed centrally on the inner side of said band whereby to provide for attachment of said sensing electrodes to said band.

6. The belt according to claim 3 further including a second fold of said band of fabric, said second fold extending from said upper edge and being folded on said band and attached to the center of said band; and a sensing electrode fastening means being attached to said second fold of said band.

7. A belt for securing sensing electrodes to the chest of an infant afflicted with Apnea, said belt comprising:

an elongated band of fabric of sufficient length to encircle and to be fastened around the chest of said infant, said band having an inner side and an outer side and two ends;

tunnel means disposed on said band, said tunnel means being a fold of said band and extending over the entire length of said belt and adapted to removably receive and house wires for connecting sensing electrodes to a monitor;

first and second port means disposed in said tunnel means, said first port means being formed as openings at each end of said band to allow wires to extend from each of the ends of said band and be connected to said monitor, said second port means disposed centrally about said band, said second port means being arranged to allow wires to extend from said band to connect to said sensing electrodes;

an interrelated, two component, adjustable fastener means disposed on each end of said band, one of the two components of said fastener means being disposed on the inner side of said band and the other of said components being disposed on the outer side of said band, whereby the components of the fastener means can overlap and attach to each other to form an adjustable belt that can be fastened over the back of the infant and provide for disposition of said sensing electrodes on the chest of said infant and whereby said wires can emerge from a rear of the belt when worn.

* * * * *